United States Patent
Im et al.

(10) Patent No.: US 9,801,876 B2
(45) Date of Patent: Oct. 31, 2017

(54) COMPLEX GRANULE FORMULATION HAVING IMPROVED STABILITY COMPRISING LEVOCETIRIZINE AND MONTELUKAST

(71) Applicant: HANMI PHARM. CO., LTD, Hwaseong-si, Gyeonggi-do (KR)

(72) Inventors: Ho Taek Im, Yongin-si (KR); Taek Kwan Kwon, Suwon-si (KR); Yong Il Kim, Suwon-si (KR); Jae Hyun Park, Suwon-si (KR); Jong Soo Woo, Suwon-si (KR)

(73) Assignee: HANMI PHARM. CO., LTD, Hwaseong-Si (KR)

( * ) Notice: Subject to any disclaimer, the term of this patent is extended or adjusted under 35 U.S.C. 154(b) by 0 days.

(21) Appl. No.: 14/898,935

(22) PCT Filed: Jun. 16, 2014

(86) PCT No.: PCT/KR2014/005266
§ 371 (c)(1),
(2) Date: Dec. 16, 2015

(87) PCT Pub. No.: WO2014/208915
PCT Pub. Date: Dec. 31, 2014

(65) Prior Publication Data
US 2016/0367551 A1    Dec. 22, 2016

(30) Foreign Application Priority Data

Jun. 28, 2013 (KR) .................. 10-2013-0075099
Mar. 31, 2014 (KR) .................. 10-2014-0037540

(51) Int. Cl.
| *A61K 31/497* | (2006.01) |
| *A61K 31/47* | (2006.01) |
| *A61K 31/495* | (2006.01) |
| *A61K 9/16* | (2006.01) |

(52) U.S. Cl.
CPC .......... *A61K 31/495* (2013.01); *A61K 9/1623* (2013.01); *A61K 9/1652* (2013.01); *A61K 9/1694* (2013.01); *A61K 31/47* (2013.01)

(58) Field of Classification Search
CPC .............................. A61K 31/495; A61K 31/47
USPC ............................................ 514/252.12, 311
See application file for complete search history.

(56) References Cited

U.S. PATENT DOCUMENTS 5,866,162 A    2/1999    Grattan

FOREIGN PATENT DOCUMENTS

| KR | 10-2013-0009553 A | 1/2013 |
| WO | 2010/107404 A1 | 9/2010 |
| WO | 2011/110939 A2 | 9/2011 |
| WO | 2012/064304 A2 | 5/2012 |

OTHER PUBLICATIONS

International Searching Authority, International Search Report of PCT/KR2014/005266 dated Sep. 23, 2014.

*Primary Examiner* — Raymond Henley, III
(74) *Attorney, Agent, or Firm* — Sughrue Mion, PLLC

(57) ABSTRACT

The present invention relates to a complex granule formulation comprising a first granular part comprising levocetirizine or its pharmaceutically acceptable salt, cyclodextrin or its derivative, and an alkalinizing agent; and a second granular part comprising montelukast or its pharmaceutically acceptable salt, cyclodextrin or its derivative, and an alkalinizing agent. This formulation can effectively inhibit the production of related compounds of levocetirizine and montelukast by allowing levocetirizine and montelukast to form clathrate complexes with cyclodextrin, and using an alkalinizing agent. This formulation not only shows increased stability and bioavailability, but also improves patient compliance owing to its effective masking of bitter taste.

8 Claims, 11 Drawing Sheets

COMPLEX GRANULE FORMULATION HAVING IMPROVED STABILITY COMPRISING LEVOCETIRIZINE AND MONTELUKAST

CROSS REFERENCE TO RELATED APPLICATIONS

This application is a National Stage of International Application No. PCT/KR2014/005266 filed Jun. 16, 2014 claiming priority based on Korean Patent Application Nos. 10-2013-0075099 filed Jun. 28, 2013, and 10-2014-0037540 filed Mar. 31, 2014, the contents of which are incorporated herein by reference in their entirety.

FIELD OF THE INVENTION

The present invention relates to a complex granule formulation having improved stability and bioavailability comprising levocetirizine and montelukast for the prevention or treatment of allergic rhinitis and asthma.

BACKGROUND OF THE INVENTION

It is estimated that about 300 million people worldwide suffer from asthma. Although it is not easy to compare prevalence rates of one disease among different regions, the global prevalence of asthma ranges from 1% to 18% of the population in different countries, according to an investigation conducted by a standard investigation method on children and adults.

Asthma is a common chronic, allergic inflammatory disease of the airways that many cells and various mediators are involved. The inflammation of the airways is related with hyperreactivity of the airways, causing symptoms such as recurrent wheezing, difficulty in breathing, chest discomfort, severe coughing, etc. Asthma can be defined by its clinical, physiological, and pathological characteristics. According to its clinical definition, a disease that comes with repeated breathing problem, recurrent wheezing, and coughing; in physiological definition, a hyperreactivity of the airways and partially reversible airway obstruction; and pathologically, a chronic, allergic inflammation of the airways.

Allergic rhinitis refers to a symptomatic disorder of the nose induced by an IgE-mediated inflammation after allergen exposure of the membrane of the nose. Symptoms of allergic rhinitis include rhinorrhea, nasal obstruction, nasal itching, sneezing, ocular pruritis, etc.

Allergic rhinitis and asthma can develop separately. However, there is a study showing that 58% of patients with allergic rhinitis have asthma and 85 to 95% of patients with asthma also suffer from allergic rhinitis, having high rates of complications between these two patient groups. Thus, there has been a need for developing a complex formulation which has improved stability and efficacy for the treatment of these two conditions.

Meanwhile, cetirizine is (2-(4-((4-chlorophenyl)phenylmethyl)-1-piperazinyl)ethoxy)acetic acid, and its levorotatory and dextrorotatory mirror image enantiomers are known as "levocetirizine" and "dextrocetirizine," respectively.

Levocetirizine can be obtained via breakdown or asymmetric synthesis using a racemic mixture of cetirizine, e.g., conventional methods such as published in GB Pat. No. 2,225,321 or a yeast biocatalytic hydrolysis as published in U.S. Pat. Nos. 4,800,162 and 5,057,427. Levocetirizine possesses antihistamine properties, and hence is useful as an antiallergic, an antihistamine agent, as well as an anticonvulsant and a bronchodialator. Also, levocetirizine dihydrochloride has been approved for treating allergic rhinitis and sold under Xyzal (Yuhan Corporation).

Meanwhile, montelukast is an antagonist for cysteinyl leukotriene receptor (CysLT1) which is used for the prevention and treatment of a leukotriene-mediated disease. In addition, montelukast is useful in the treatment of allergic rhinitis, atopic dermatitis, chronic urticaria, sinusitis, nasal polyp, chronic obstructive pulmonary disease, conjunctivitis including nasal conjunctivitis, migraine, cyst fibrosis, viral bronchiolitis and the like (see S. E. Dahlen, *Eur. J. Pharmacol.*, 533(1-3), 40-56(2006)).

Levocetirizine and montelukast each exhibits different therapeutic mechanisms, and they together can bring about a synergistic effect in the treatment of allergic rhinitis or asthma. Also, as the number of infants, children and elderly patients who are taking these medicines increases, there is an increasing demand for development of a complex granule formulation which may help improving patients' compliance with levocetirizine and montelukast, and for improving the stability of these two compounds that are relatively unstable.

Levocetirizine shows instability in physiochemical property, and it is difficult to maintain stability over time. There are three major degradation products of levocetirizine: related compound A (Formula I), related compound B (Formula II) and related compound E (Formula III). Related compounds A and B are created via hydrolysis of levocetirizine. Moreover, levocetirizine hydrochloride also has a drawback due to its bitter taste which lowers patient compliance.

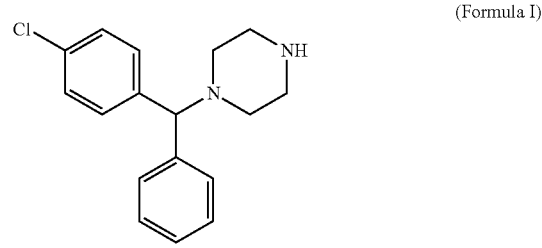

(Formula I)

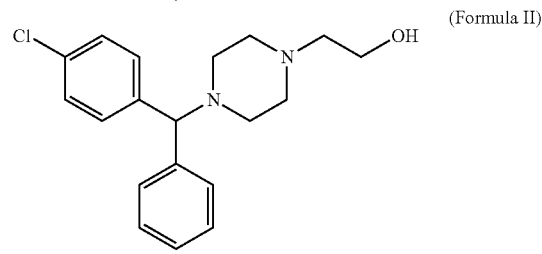

(Formula II)

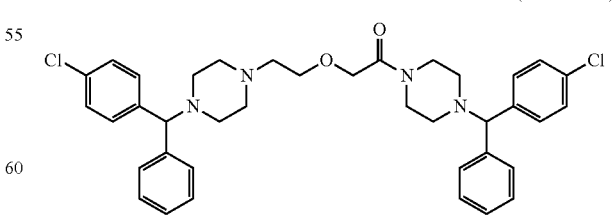

(Formula III)

Montelukast is also unstable over time. For example, according to M. M. Al Omani et al., montelukast in a solid or liquid state is known to be unstable when exposed to light, moisture and heat, and yields degradation products such as montelukast sulfoxide (Formula IV) and montelukast cis-isomer (Formula V) (*Journal of Pharmaceutical and Biomedical Analysis*, 45, 2007, 465-471). Further, it has been reported that when a commercially available Singulair chewable tablet was exposed to sunlight, the amount of montelukast sulfoxide was increased by 2.4% after 3 weeks; and when montelukast in 0.1 M hydrochloric acid solution was exposed to a sodium vapor lamp for 6 hours, the amount of montelukast cis-isomer was increased by 14.6%.

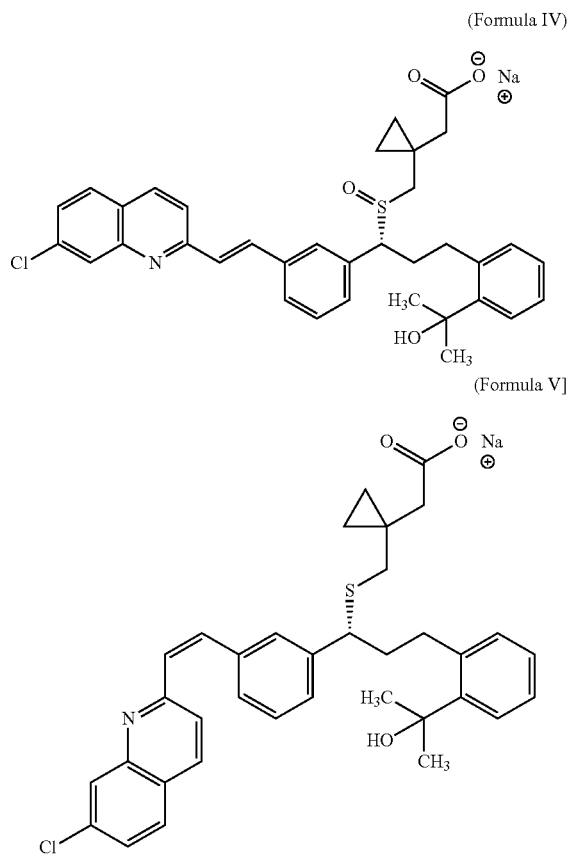 [SMILES: CC(C)(O)c1ccccc1CC[C@H](c1cccc(/C=C/c2ccc3ccc(Cl)cc3n2)c1)S(=O)CC1(CC(=O)[O-])CC1 ; [Na+] ; CC(C)(O)c1ccccc1CC[C@@H](SCC1(CC(=O)[O-])CC1)c1cccc(/C=C\c2ccc3ccc(Cl)cc3n2)c1 ; [Na+]]

(Formula IV)

(Formula V)

The inventors of the present invention have conducted a research on a complex formulation comprising levocetirizine and montelukast as active ingredients. Due to the physicochemical properties of these compounds, however, there were difficulties in storage and administration of such formulation. When prepared in the form of a tablet, there remained a problem of reduced patient compliance in patients having difficulties in swallowing or chewing or those who do not prefer such type of formulation, e.g., children.

SUMMARY OF THE INVENTION

Therefore, it is an object of the present invention to provide a taste-masked complex granule formulation having improved stability and good bioavailability comprising levocetirizine and montelukast.

In accordance with one object of the present invention, there is provided a complex granule formulation comprising (a) a first granular part comprising levocetirizine or its pharmaceutically acceptable salt, cyclodextrin or its derivative, and an alkalinizing agent; and (b) a second granular part comprising montelukast or its pharmaceutically acceptable salt, cyclodextrin or its derivative, and an alkalinizing agent.

A complex granule formulation according to the present invention contains levocetirizine and montelukast, each of which forms clathrate complexes with cyclodextrin, and employs an alkalinizing agent. Thus, any possible contact between two main ingredients can be prevented; the production of related compounds can be inhibited during a long-term storage; and bioavailability of the active ingredients can be improved as well. Moreover, the bitter taste of levocetirizine can be masked so as to improve patient compliance.

DETAILED DESCRIPTION OF THE INVENTION

Figure 1:
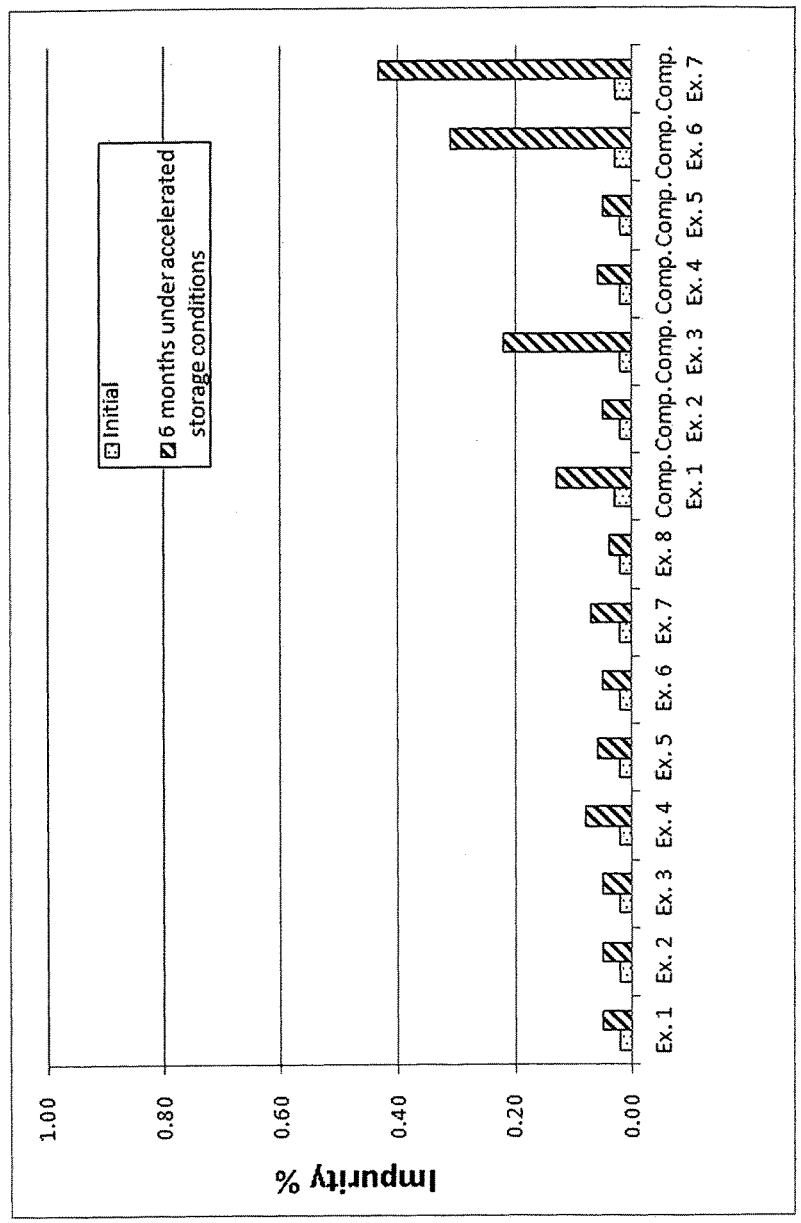
FIG. 1 shows the result of a stability test of complex granule formulations obtained in Examples 1 to 8 and Comparative Examples 1 to 7, comparing the amount of levocetirizine related compound A produced under accelerated condition (40° C./75% RH) for 6 months with its initial amount.
Figure 2:
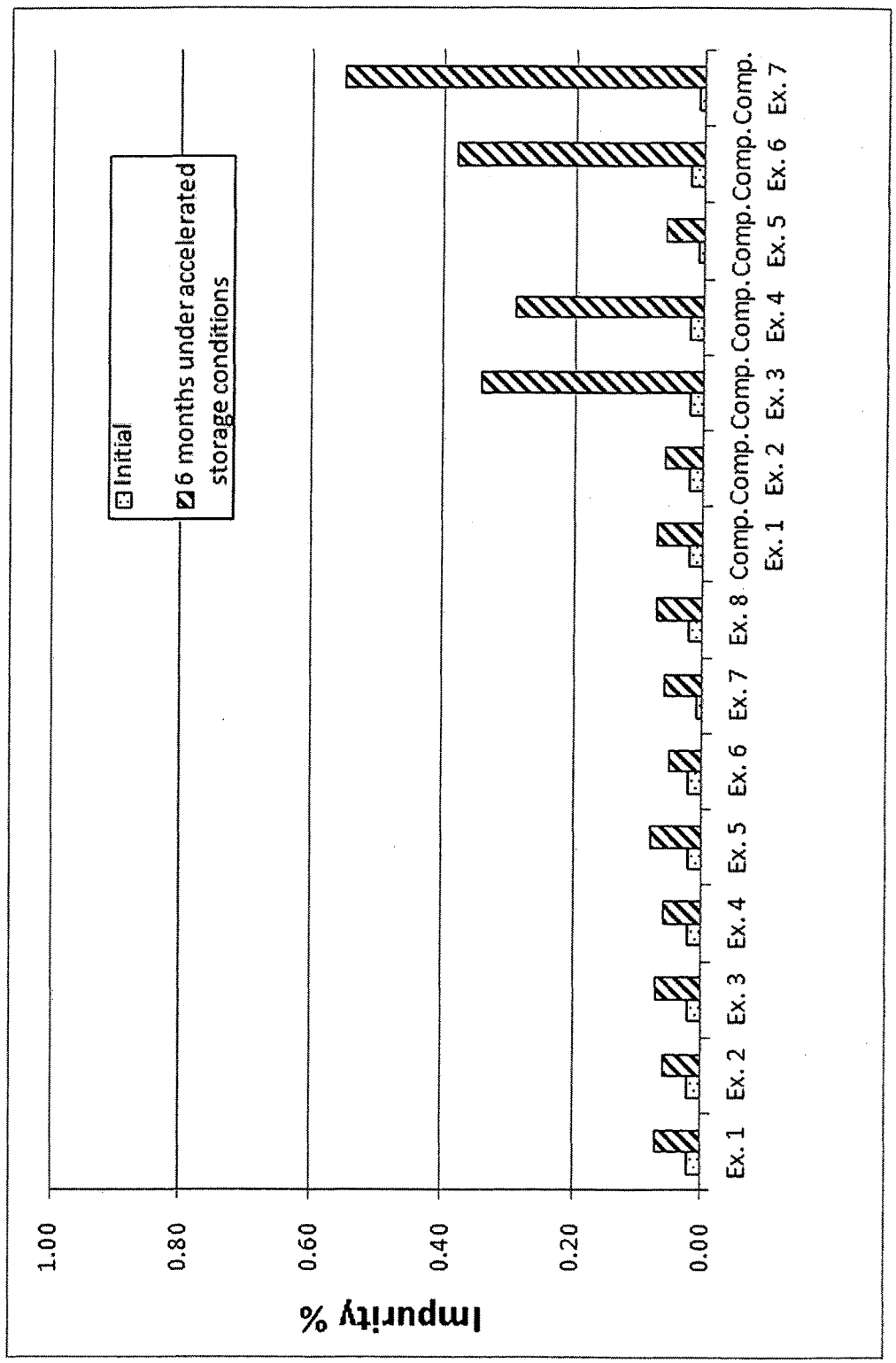
FIG. 2 shows the result of a stability test of complex granule formulations obtained in Examples 1 to 8 and Comparative Examples 1 to 7, comparing the amount of levocetirizine related compound B produced under accelerated condition (40° C./75% RH) for 6 months with its initial amount.
Figure 3:
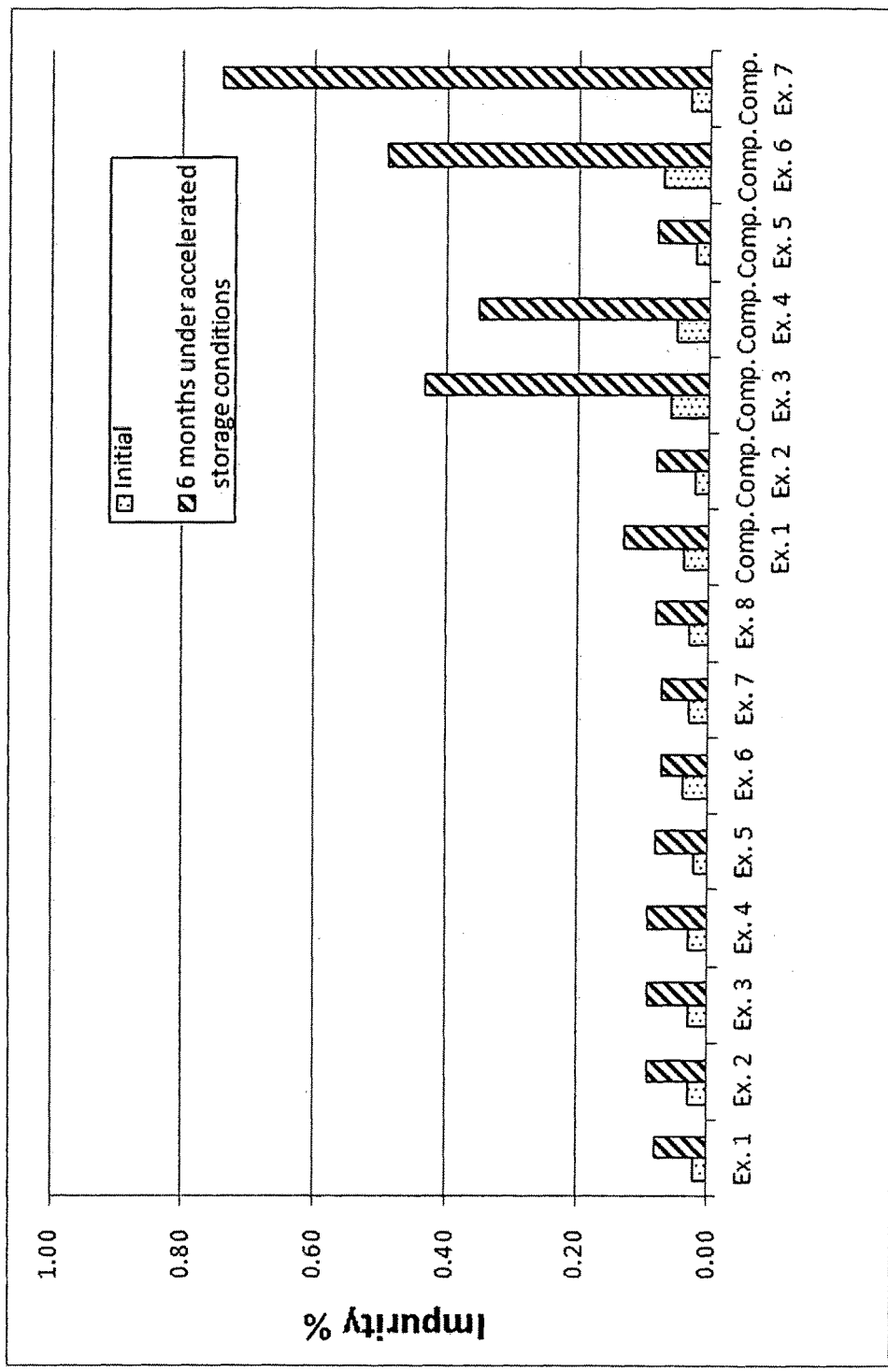
FIG. 3 shows the result of a stability test of complex granule formulations obtained in Examples 1 to 8 and Comparative Examples 1 to 7, comparing the amount of levocetirizine related compound E produced under accelerated condition (40° C./75% RH) for 6 months with its initial amount.
Figure 4:
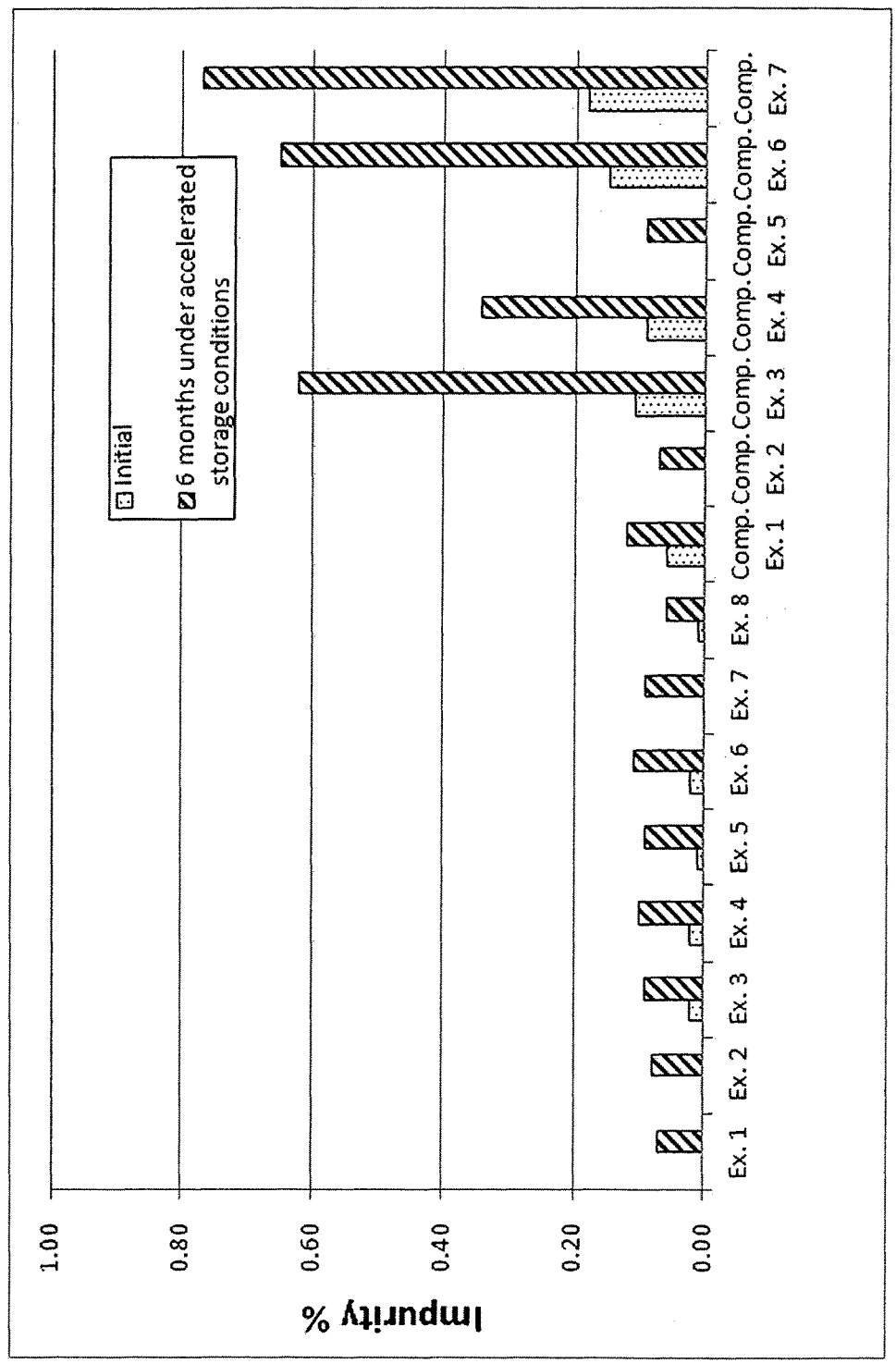
FIG. 4 shows the result of a stability test of complex granule formulations obtained in Examples 1 to 8 and Comparative Examples 1 to 7, comparing the amount of unknown levocetirizine related compound (RRT=0.59) produced under accelerated condition (40° C./75% RH) for 6 months with its initial amount.
Figure 5:
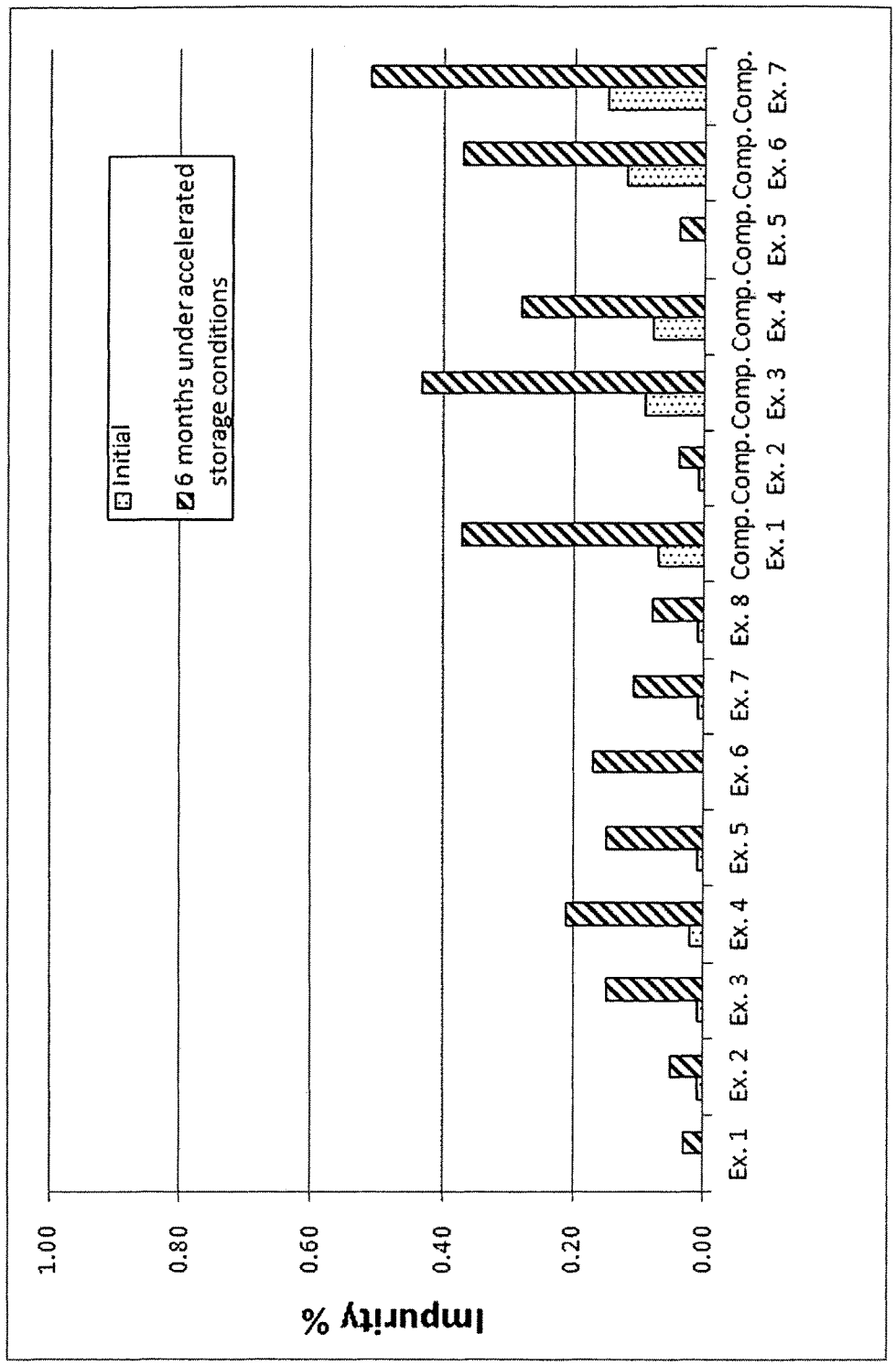
FIG. 5 shows the result of a stability test of complex granule formulations obtained in Examples 1 to 8 and Comparative Examples 1 to 7, comparing the amount of unknown levocetirizine related compound (RRT=0.64) produced under accelerated condition (40° C./75% RH) for 6 months with its initial amount.
Figure 6:
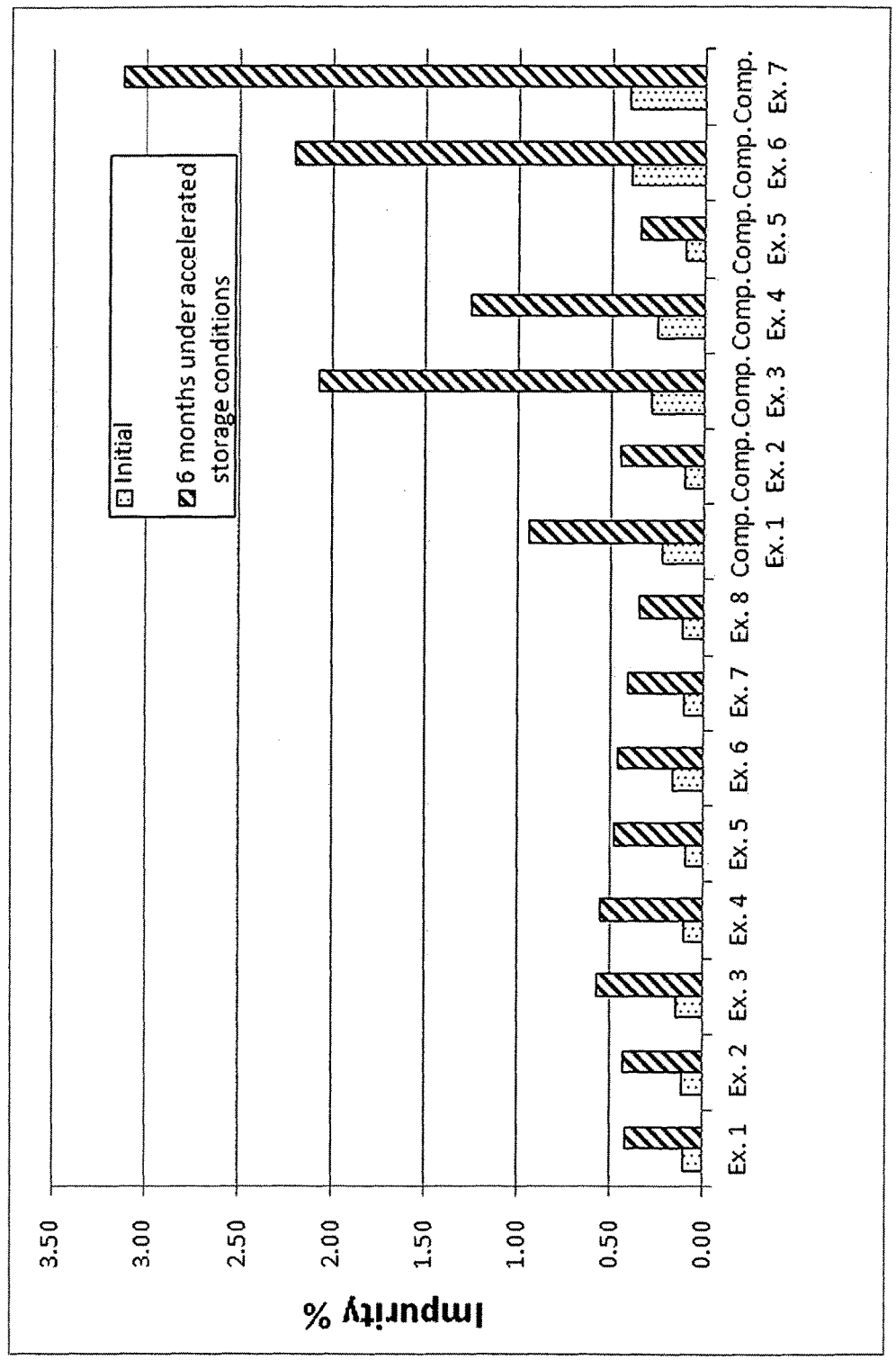
FIG. 6 shows the result of a stability test of complex granule formulations obtained in Examples 1 to 8 and Comparative Examples 1 to 7, comparing the total amount of levocetirizine related compounds produced under accelerated condition (40° C./75% RH) for 6 months with their initial amount.
Figure 7:
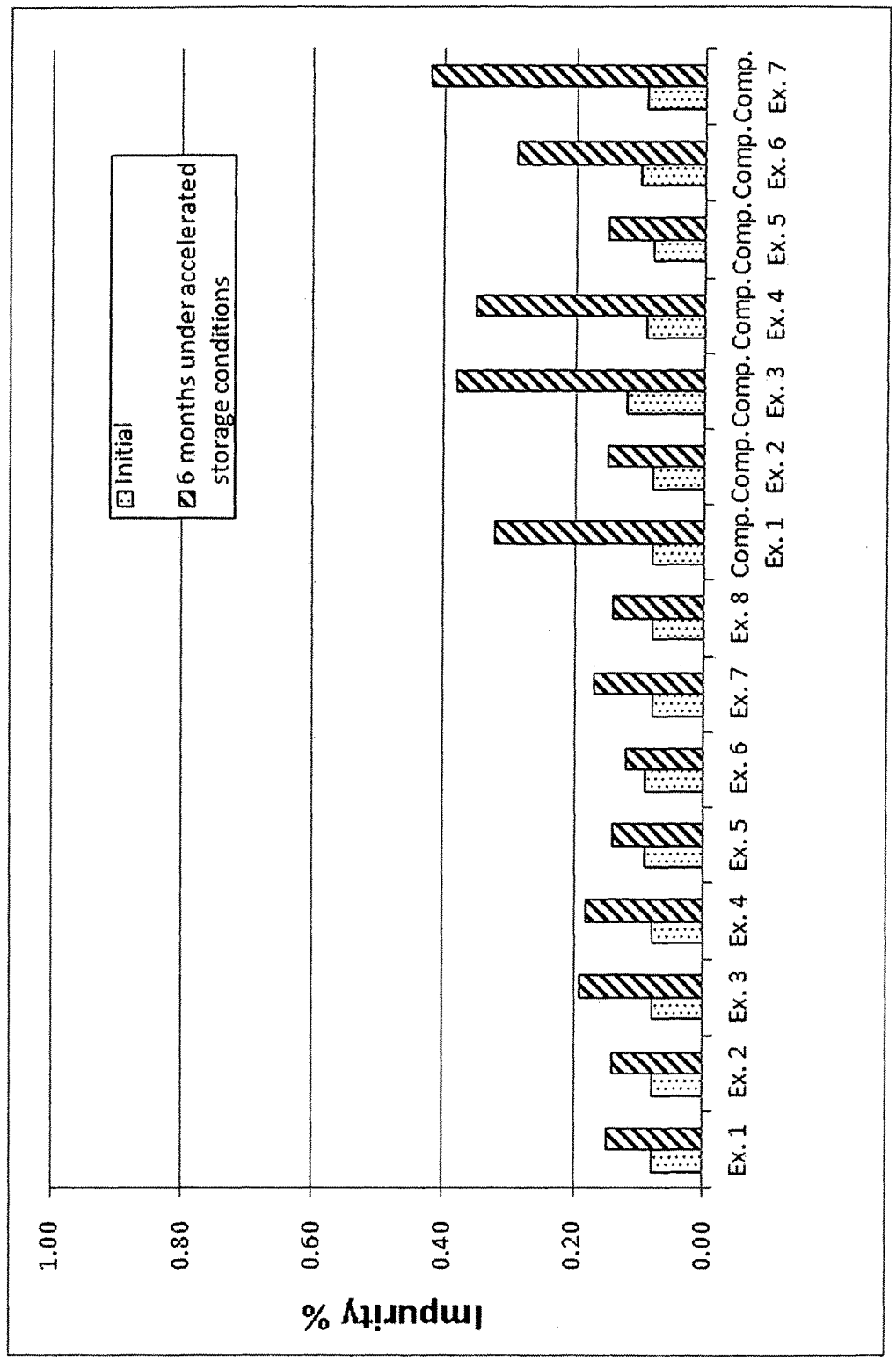
FIG. 7 shows the result of a stability test of complex granule formulations obtained in Examples 1 to 8 and Comparative Examples 1 to 7, comparing the amount of montelukast sulfoxide produced under accelerated condition (40° C./75% RH) for 6 months with its initial amount.
Figure 8:
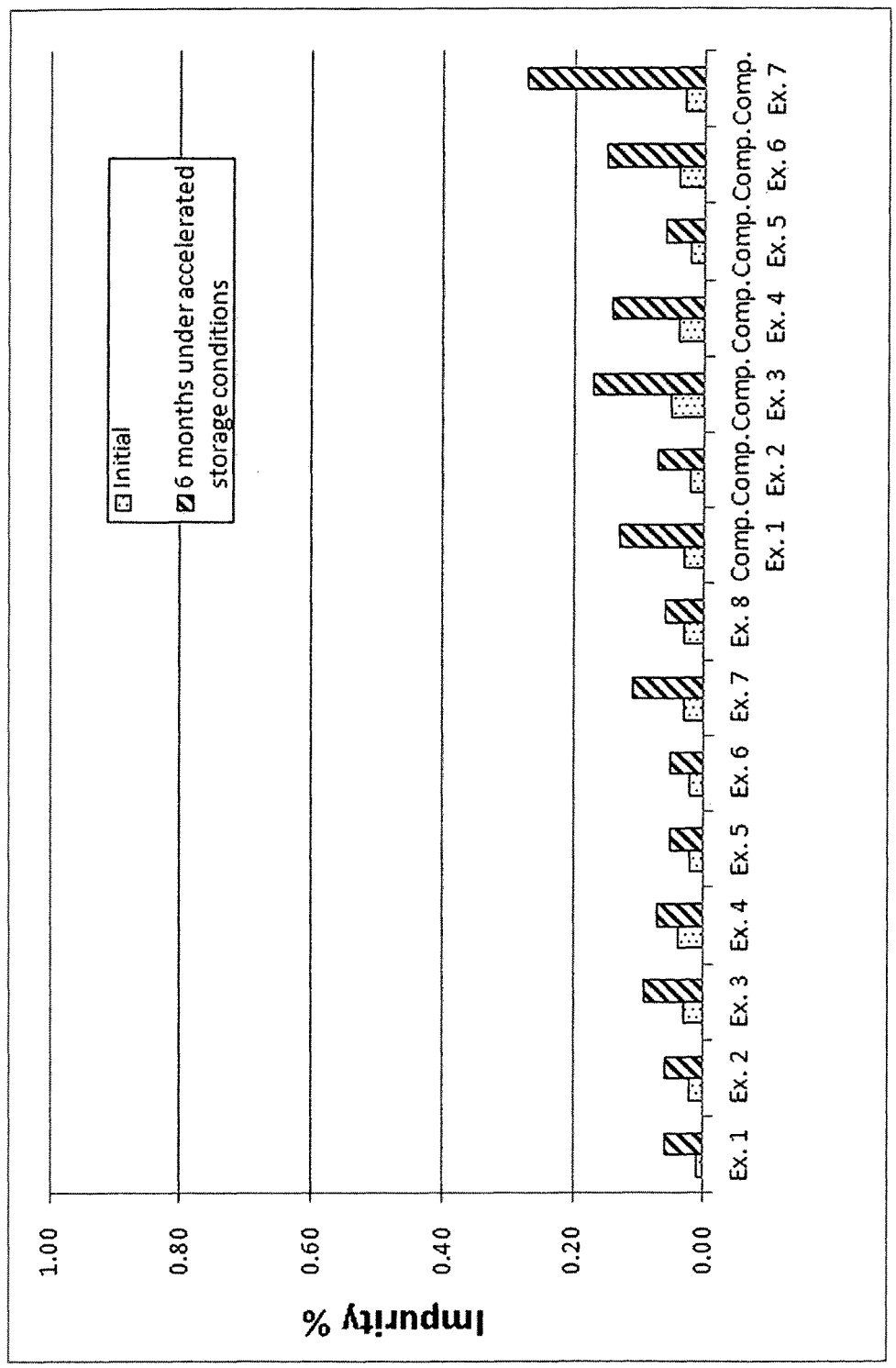
FIG. 8 shows the result of a stability test of complex granule formulations obtained in Examples 1 to 8 and Comparative Examples 1 to 7, comparing the amount of montelukast cis-isomer produced under accelerated condition (40° C./75% RH) for 6 months with its initial amount.
Figure 9:
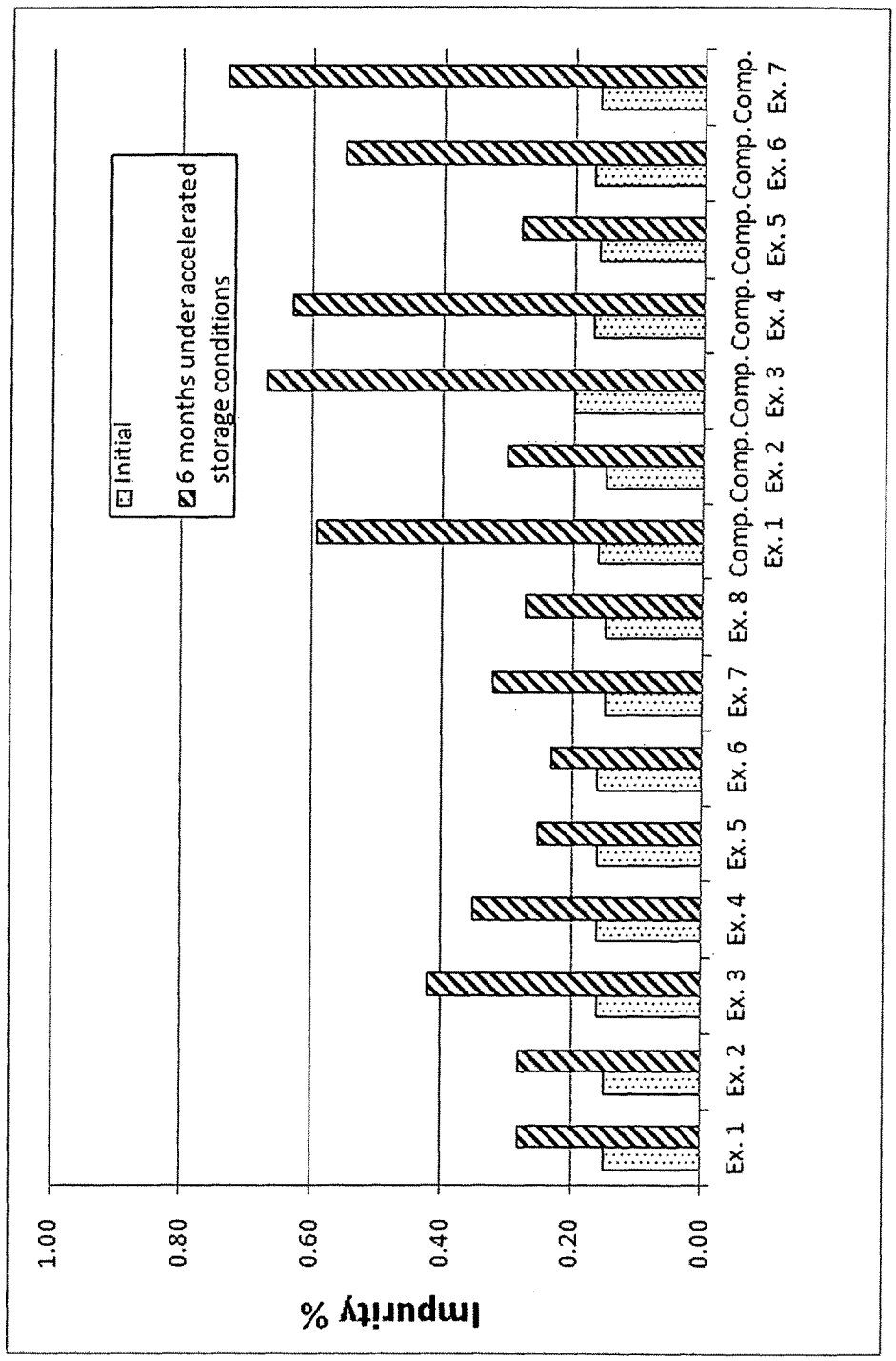
FIG. 9 shows the result of a stability test of complex granule formulations obtained in Examples 1 to 8 and Comparative Examples 1 to 7, comparing the amount of montelukast related compounds produced under accelerated condition (40° C./75% RH) for 6 months with their initial amount.

The present invention is explained in detail hereinafter.

The present invention provides a complex granule formulation comprising (a) a first granular part comprising levocetirizine or its pharmaceutically acceptable salt, cyclodextrin or its derivative, and an alkalinizing agent; and (b) a second granular part comprising montelukast or its pharmaceutically acceptable salt, cyclodextrin or its derivative, and an alkalinizing agent.

A complex granule formulation according to the present invention employs an antihistamine agent (levocetirizine) as a first active ingredient to effectively reduce early responses of allergic rhinitis or asthma, and as an anti-leukotriene agent (montelukast) as a second active ingredient for the treatment or prevention of asthma and one of the major symptoms of late allergic rhinitis, i.e., nasal obstruction.

A complex granule formulation of the present invention contains the following parts.

A. First Granular Part (1) Levocetirizine or its Pharmaceutically Acceptable Salt In the present invention, levocetirizine or a pharmaceutically acceptable salt thereof contained in the first granular part as an active ingredient is, for instance, disclosed in EP Pat. Nos. 0,058,146, 0,601,028 and 0,801,064, GB Pat. Nos. 2,225,320 and 2,225,321, U.S. Pat. No. 5,478,941 and WO 97/37982.

Examples of a pharmaceutically acceptable salt of levocetirizine include non-toxic, inorganic and organic acid addition salts of acetic acid, citric acid, maleic acid, succinic acid, ascorbic acid, hydrochloric acid, hydrobromic acid, sulfuric acid, phosphoric acid and the like, metallic acid thereof (e.g., sodium salt or calcium salt), ammonium salt, amine salt and amino acid salt, preferably levocetirizine dihydrochloride salt. The daily dosage amount of levocetirizine or a pharmaceutically acceptable salt thereof is 0.4 to 100 mg, preferably 1 to 50 mg, more preferably 2.5 to 20 mg.

(2) Cyclodextrin or its Derivative

Cyclodextrins (CDs) are cyclic oligosaccharides composed of 6 to 12 D-glucose units connected via α-1,4-glucosidic linkages to form a cylindrically shaped compound. Secondary hydroxyl groups of $C_2$—OH and $C_3$—OH are located on the side of wider mouth part of the cylinder of cyclodextrin, and primary hydroxyl groups of $C_6$—OH can be found on the other side of smaller mouth part. The outer side of the cylinder is hydrophilic, whereas the inner side of the cylinder shows hydrophobic character due to the presence of hydrogen atoms.

There is a number of different cyclodextrins depending on the degree of polymerization of D-glucose units in the molecular circle; six glucose units yield α-cyclodextrin; seven units, β-cyclodextrin; eight units, γ-cyclodextrin. In one embodiment of the present invention, β-cyclodextrin is used; and β-cyclodextrin derivatives, e.g., hydroxypropyl β-cyclodextrin, may also be used.

The cyclodextrin may be used in an amount of 3 to 7 wt % based on the total weight of the levocetirizine granular part. When the cyclodextrin is used in an amount of at least 3 wt % based on the total weight of the levocetirizine granular part, clathrate effect is maximized, and thus a uniform and more stable clathrate may be formed. When the cyclodextrin is used in an amount greater than 7 wt % based on the total weight of the levocetirizine granular part, however, drawbacks such as excessive volume of the formulation or difficulties in manufacturing the formulation may occur due to an excessive amount of cyclodextrin as compared to the amount of pharmacologically active levocetirizine. Also, excessive cyclodextrin is not completely dissolved during the manufacturing process and it undesirably hinders masking of bitter taste.

(3) Alkalinizing Agent

In accordance with a formulation of the present invention, the first granular part contains an alkalinizing agent as a stabilizing agent (or pH regulator). The alkalinizing agent not only improves the stabilities of drugs from related compound by maintaining the inside of the granular part at a neutral or basic condition, but also makes the manufacturing process easier by increasing the solubility of montelukast when preparing a montelukast binding solution. The alkalinizing agent may be meglumine, sodium bicarbonate, sodium carbonate monohydrate, ammonia water, sodium citrate, dried sodium carbonate, or a mixture thereof. The alkalinizing agent may be used in an amount of 0.2 to 0.6 wt % based on the total weight of each granular part. If the amount of the alkalinizing agent exceeds 0.6 wt % based on the total weight of the granular part, the alkalinizing agent has no additional effect on the stabilities and it adds unpleasant feeling caused by the alkalinizing agent.

(4) Other Pharmaceutically Acceptable Additive

A first granular part of the formulation according to the present invention may further contain one or more pharmaceutically acceptable additives. The additive may be selected from the group consisting of a diluent, a sweetener, a flavor, a colorant, a binder, and a mixture thereof.

In the present invention, the diluent may be selected from the group consisting of microcrystalline cellulose, lactose, ludipress, mannitol, calcium dihydrogen phosphate, starch, low-substituted hydroxypropyl cellulose and a mixture thereof. The diluent may be employed in an amount of 1 to 99 wt %, preferably 5 to 95 wt % based on the total weight of the granular part.

In the present invention, the sweetener may be selected from the group consisting of aspartame, acesulfame salt, sucralose, saccharin salt, neotame, cyclamate, thaumatin, LuoHan Guo extract, glycyrrhizin, steviten light (at least 98% stevioside), steviten rich (100% enzymatically modified stevia), sugar, glucose, maltose, oligosaccharide, dextrin, invert sugar, fructose, lactose, galactose, corn syrup, sorbitol, maltitol, xylitol, erythritol, high fructose corn syrup and trehalose. The sweetener may be used in an amount of 0.1 to 10 wt % based on the total weight of the granular part.

Examples of the flavor of the present invention include natural flavors, synthetic flavors, and a mixture thereof. The natural flavors may be spearmint oil, cinnamon oil, peppermint oil, lemon oil, clove oil, bay oil, thyme oil, cedar leaf oil, nutmeg oil, sage oil, almond oil, and the like. Also, the synthetic flavors may be synthetic fruit flavors such as lemon, orange, grape, lime and strawberry, and synthetic flavors such as vanilla, chocolate, coffee, cocoa, pine needle, ginseng, red ginseng and citrus. The flavors may be used in an amount of 0.1 to 10 wt % based on the total weight of the granular part.

The colorant of the present invention is any colorant that has the maximum absorption wavelength in the 400 nm to 550 nm range, for example, one or more selected from the group consisting of Food Red No. 40 (maximum absorption wavelength in the 497 nm to 501 nm range), Food Yellow No. 5 (maximum absorption wavelength in the 480 nm to 484 nm), Yellow No. 4 (maximum absorption wavelength in the 426 nm to 430 nm), and a safflower yellow dye (maximum absorption wavelength at 400 nm), preferably Food Red No. 40. The colorant may be used in an amount of 0.01 to 1 wt % based on the total weight of the granular part.

The binder of the present invention may be selected from the group consisting of hydroxypropyl cellulose, hypromellose, polyvinyl pyrrolidone, copovidone, macrogol, light anhydrous silicic acid, synthetic aluminum silicate, calcium silicate or silica derivatives magnesium metasilicate aluminate, phosphate salts such as calcium phosphate dibasic, carbonate salts such as calcium carbonate, and a mixture thereof. The amount of binder employed may be, based on the total weight of the granular part, 0.5 to 30 wt %, preferably 2 to 20 wt %.

B. Second Granular Part (1) Montelukast or its Pharmaceutically Acceptable Salt

In the present invention, a pharmaceutically acceptable salt of montelukast comprised in the second granular part as an active ingredient is, for example, non-toxic, inorganic and organic acid addition salts of acetic acid, citric acid, maleic acid, succinic acid, ascorbic acid, hydrochloric acid, hydrobromic acid, sulfuric acid, phosphoric acid and the like, metal salt thereof (e.g., sodium salt or calcium salt), ammonium salt, amine salt and amino acid salt. In one embodiment, montelukast sodium is employed. The daily dosage amount of montelukast or its pharmaceutically acceptable salt is 0.4 to 100 mg, preferably 1 to 50 mg, more preferably 2.5 to 20 mg.

(2) Cyclodextrin or its Derivative

The cyclodextrin or its derivative in the second granular part of the present invention and the amount thereof are the same as described in the first granular part.

(3) Alkalinizing Agent

The alkalinizing agent in the second granular part of the present invention and the amount thereof are the same as described in the first granular part.

(4) Other Pharmaceutically Acceptable Additives

The pharmaceutically acceptable additives in the second granular part of the present invention and the amount thereof are the same as described in the first granular part.

Granules which are formed in the first and second granular parts may be further coated so as to completely separate active ingredients. The coating process may be carried out on either one of levocetirizine and montelukast granules, or both.

Coating agents that can be used in the coating process may be conventional polymers, for example, hypromellose, methyl cellulose, ethyl cellulose, polyvinyl alcohol, polyvinyl pyrrolidone, hydroxyethylcellulose, hydroxypropyl methylcellulose, but not limited thereto. The amount of the coating agent is preferably kept at minimum so as to improve efficiency in production and provide a formulation size optimal for administration. The amount is, based on the total weight of each granular part, 0.5 to 20 wt %, preferably 1 to 10 wt %.

There is no specific limitation of the mixing ratio of the first and second granular parts. The first and the second granular parts may be mixed in a weight ratio of 20:80 to 80:20, which may be administered to a patient at various dose levels.

Further, a complex granule formulation of the present invention is prepared in a package so as to protect the formulation from light and moisture. Examples of suitable packaging materials include foil (e.g., aluminum) pouch or sachet. The foil may be laminated with a polyester film, which protects children from biting and tearing the package, on its outer surface. Linear low density polyethylene may act as a heat-sealable layer for pouch.

A complex granule formulation according to the present invention may be used in the prevention or treatment of allergic rhinitis and asthma, and the allergic rhinitis may be selected from the group consisting of rhinorrhea, nasal obstruction, nasal itching, sneezing and ocular pruritis.

Meanwhile, a complex granule formulation according to the present invention may be manufactured by a method, which comprises the steps of (i) preparing a first granular part by dissolving cyclodextrin or a derivative thereof in purified water, and mixing with levocetirizine or a pharmaceutically acceptable salt thereof and an alkalinizing agent to prepare a levocetirizine binding solution, followed by granulation of the binding solution; (ii) preparing a second granular part by dissolving an alkalinizing agent in purified water, dissolving montelukast or a pharmaceutically acceptable salt thereof and then mixing with cyclodextrin or a derivative thereof to prepare montelukast binding solution, followed by granulation of the binding solution; and (iii) mixing the first and second granular parts prepared.

A complex granule formulation according to the present invention prevents a possible contact between two active ingredients by allowing each of levocetirizine and montelukast to form clathrate complexes with cyclodextrin and using an alkalinizing agent as a stabilizing agent. Thus, possible reactions among related compounds are minimized, thereby improving the stability and efficacy. Also, the complex granule formulation effectively masks the bitter taste by allowing levocetirizine to form clathrate complexes with cyclodextrin, which improves patient compliance, especially in children and elderly patients.

Hereinafter, the present invention is described more specifically by the following examples, but these are provided only for illustration purposes and the present invention is not limited thereto.

Examples 1 to 3 and Comparative Examples 1 and 2: Preparation of Complex Granule Formulations Having Various Amounts of Alkalinizing Agent Complex granule formulations were prepared by varying the amount of an alkalinizing agent listed in the Table 1 below.

Specifically, hydroxypropyl β-cyclodextrin, different amounts of meglumine, and levocetirizine dihyhydrochloride were, in sequence, dissolved in distilled water to prepare a levocetirizine binding solution. The binding solution thus obtained was mixed with D-mannitol, dried, and then sieved to obtain a levocetirizine granular part.

Meanwhile, various amounts of meglumine were dissolved in distilled water, and montelukast and hydroxypropyl β-cyclodextrin were sequentially added thereto to prepare a binding solution. Since montelukast has a low aqueous solubility, meglumine was dissolved first for easier dissolution of montelukast. The binding solution thus obtained was mixed with D-mannitol, dried, and then sieved to obtain a montelukast granular part.

The two granular parts thus obtained were mixed in a same proportion, packaged in a sachet per unit dosage to prepare complex granule formulations comprising 5 mg of montelukast and 5 mg of levocetirizine.

TABLE 1

| Component | Ingredient | Ex. 1 | Ex. 2 | Ex. 3 | Comp. Ex. 1 | Comp. Ex. 2 |
|---|---|---|---|---|---|---|
| Levocetirizine granular part (mg) | Levocetirizine dihydrochloride | 5.0 | 5.0 | 5.0 | 5.0 | 5.0 |
| | Meglumine | 3.0 | 2.0 | 1.0 | — | 4.0 |
| | Hydroxypropyl β-cyclodextrin | 30.0 | 30.0 | 30.0 | 30.0 | 30.0 |
| | D-mannitol | 462.0 | 463.0 | 464.0 | 465.0 | 465.0 |
| | Distilled water | <40.0> | <40.0> | <40.0> | <40.0> | <40.0> |
| | Total weight of the part | 500.0 | 500.0 | 500.0 | 500.0 | 500.0 |
| Montelukast granular part (mg) | Montelukast sodium | 5.2 | 5.2 | 5.2 | 5.2 | 5.2 |
| | Meglumine | 3.0 | 2.0 | 1.0 | — | 4.0 |
| | Hydroxypropyl β-cyclodextrin | 30.0 | 30.0 | 30.0 | 30.0 | 30.0 |
| | D-mannitol | 461.8 | 462.8 | 463.8 | 464.8 | 464.8 |
| | Distilled water | <40.0> | <40.0> | <40.0> | <40.0> | <40.0> |
| | Total weight of the part | 500.0 | 500.0 | 500.0 | 500.0 | 500.0 |

Example 4 and Comparative Examples 3 to 5: Preparation of Complex Granule Formulations Having Various Amounts of Cyclodextrin According to the composition and the amount described in Table 2 below, complex granule formulations were prepared by repeating the procedures of Example 1, except changing the amount of hydroxypropyl β-cyclodextrin of Example 1, to obtain complex granule formulations of Example 4 and Comparative Examples 3 to 5.

TABLE 2

| Component | Ingredient | Comp. Ex. 3 | Comp. Ex. 4 | Ex. 4 | Comp. Ex. 5 |
|---|---|---|---|---|---|
| Levocetirizine granular part (mg) | Levocetirizine dihydrochloride | 5.0 | 5.0 | 5.0 | 5.0 |
| | Meglumine | 3.0 | 3.0 | 3.0 | 3.0 |
| | Hydroxypropyl β-cyclodextrin | — | 10.0 | 20.0 | 40.0 |
| | D-mannitol | 492.0 | 482.0 | 472.0 | 452.0 |
| | Distilled water | <40.0> | <40.0> | <40.0> | <40.0> |
| | Total weight of the part | 500.0 | 500.0 | 500.0 | 500.0 |
| Montelukast granular part (mg) | Montelukast sodium | 5.2 | 5.2 | 5.2 | 5.2 |
| | Meglumine | 3.0 | 3.0 | 3.0 | 3.0 |
| | Hydroxypropyl β-cyclodextrin | — | 10.0 | 20.0 | 40.0 |
| | D-mannitol | 491.8 | 481.8 | 471.8 | 451.8 |
| | Distilled water | <40.0> | <40.0> | <40.0> | <40.0> |
| | Total weight of the part | 500.0 | 500.0 | 500.0 | 500.0 |

Examples 5 to 8 and Comparative Example 6: Preparation of Complex Granule Formulations Having Various Amounts of Main Ingredients and Alkalinizing Agent According to the composition and the amount described in Table 3 below, complex granule formulations were prepared by repeating the procedures of Example 1, except changing the amount of the main ingredient and the type of the alkalinizing agent of Example 1, to obtain complex granule formulations of Example 5 to 8 and Comparative Example 6.

TABLE 3

| Component | Ingredient | Ex. 5 | Ex. 6 | Ex. 7 | Ex. 8 | Comp. Ex. 6 |
|---|---|---|---|---|---|---|
| Levocetirizine granular part (mg) | Levocetirizine dihydrochloride | 2.5 | 1.25 | 5.0 | 5.0 | 5.0 |
|  | Meglumine | 3.0 | 3.0 | — | — | — |
|  | Sodium citrate | — | — | 3.0 | — | — |
|  | Sodium bicarbonate | — | — | — | 3.0 | — |
|  | Sodium hydroxide | — | — | — | — | 3.0 |
|  | Hydroxypropyl β-cyclodextrin | 30.0 | 30.0 | 30.0 | 30.0 | 30.0 |
|  | D-mannitol | 464.5 | 465.75 | 462.0 | 462.0 | 462.0 |
|  | Distilled water | <40.0> | <40.0> | <40.0> | <40.0> | <40.0> |
|  | Total weight of the part | 500.0 | 500.0 | 500.0 | 500.0 | 500.0 |
| Montelukast granular part (mg) | Montelukast sodium | 4.16 | 4.16 | 5.2 | 5.2 | 5.2 |
|  | Meglumine | 3.0 | 3.0 | — | — | — |
|  | Sodium citrate | — | — | 3.0 | — | — |
|  | Sodium bicarbonate | — | — | — | 3.0 | — |
|  | Sodium hydroxide | — | — | — | — | 3.0 |
|  | Hydroxypropyl β-cyclodextrin | 30.0 | 30.0 | 30.0 | 30.0 | 30.0 |
|  | D-mannitol | 462.84 | 462.84 | 461.8 | 461.8 | 461.8 |
|  | Distilled water | <40.0> | <40.0> | <40.0> | <40.0> | <40.0> |
|  | Total weight of the part | 500.0 | 500.0 | 500.0 | 500.0 | 500.0 |

Comparative Example 7: Preparation of Complex Granule Formulation Having Levocetirizine and Montelukast in Same Granules According to the composition and the amount described in Table 4 below, a complex granule formulation was prepared.

Specifically, hydroxypropyl β-cyclodextrin, meglumine, and levocetirizine were, in sequence, dissolved in distilled water to prepare a levocetirizine binding solution.

Separately, meglumine was dissolved in distilled water, and then montelukast and hydroxypropyl β-cyclodextrin were, in sequence, dissolved in the solution to obtain a montelukast binding solution.

The two binding solution thus prepared were mixed first, further mixed with D-mannitol, dried and sieved to obtain granules comprising levocetirizine and montelukast. The granules thus obtained were packaged in a sachet to prepare a complex granule formulation comprising 5 mg of montelukast and 5 mg of levocetirizine.

TABLE 4

|  |  | Comp. Ex. 7 |
|---|---|---|
| Levocetirizine granular part (mg) | Levocetirizine dihydrochloride | 5.0 |
|  | Meglumine | 3.0 |
|  | Hydroxypropyl β-cyclodextrin | 30.0 |
|  | D-mannitol | 462.0 |
|  | Distilled water | <40.0> |
|  | Total weight of the part | 500.0 |
| Montelukast granular part (mg) | Montelukast sodium | 5.2 |
|  | Meglumine | 3.0 |
|  | Hydroxypropyl β-cyclodextrin | 30.0 |
|  | D-mannitol | 461.8 |
|  | Distilled water | <40.0> |
|  | Total weight of the part | 500.0 |

Experimental Example 1: Stability Test Under Accelerated Storage Conditions

Complex granule formulations prepared in Examples 1 to 8 and Comparative Examples 1 to 7 were stored under accelerated conditions as follows. The amount of related compounds of montelukast and levocetirizine was evaluated to compare the stability of the complex granule formulations. The results are shown in Tables 7 to 10, and FIGS. 1 to 9.

Accelerated Storage Conditions

Storage conditions: contained as sachet packages at 40° C., 75% RH

Test duration: Initial and 6 months

Analysis target: Levocetirizine and related compounds thereof, montelukast and related compounds thereof Analysis Conditions of Levocetirizine and Levocetirizine Related Compounds Column: HPLC Symmetry RP18 column (4.6 mm×25 cm; Waters) packaged with octadecylsilyl silica gel (5 μm)

Eluents: A—DW:Acetonitrile:10% TFA=69:30:1 (v/v)
B—DW:Acetonitrile:10% TFA=29:70:1 (v/v)

TABLE 5

| | Elution conditions | |
|---|---|---|
| Time (min) | A (%) | B (%) |
| 0 | 100 | 0 |
| 2 | 100 | 0 |
| 30 | 25 | 75 |
| 40 | 100 | 0 |
| 50 | 100 | 0 |

Detector: UV-absorption detector (absorbance at 230 nm)
Flow rate 1.0 mL/min
Column temperature: 30° C.

Analysis Conditions of Montelukast and Montelukast Related Compounds

Column: HPLC LUNA Phenyl-Hexyl column (4.6 mm×10 cm; Phenomenex) packaged with phenyl-hexyl silica gel (3 μm)

Eluents: A—DW with 0.2% trifluoroacetate
B—Methanol:Acetonitrile=60:40 (v/v)

TABLE 6

| | Elution conditions | |
|---|---|---|
| Time (min) | A (%) | B (%) |
| 0 | 48 | 52 |
| 5 | 45 | 55 |
| 12 | 45 | 55 |
| 22 | 25 | 75 |
| 23 | 25 | 75 |
| 25 | 48 | 52 |
| 30 | 48 | 52 |

Detector: UV-absorption detector (absorbance at 255 nm)
Flow rate 1.5 mL/min
Column temperature: 50° C.

The content changes of levocetirizine related compounds A, B, and E are shown in Tables 7 and 8, and the content changes of montelukast related compounds, i.e., montelukast sulfoxide and montelukast cis-isomer, are shown in Tables 9 and 10.

TABLE 7

Initial amount of levocetirizine related compounds

| | Initial | | | | | |
|---|---|---|---|---|---|---|
| Formulation | Related compound A (%) | Related compound B (%) | Related compound E (%) | Unknown related compound RRT = 0.59 (%) | Unknown related compound RRT = 0.64 (%) | Total (%) |
| Ex. 1 | 0.02 | 0.02 | 0.02 | 0.00 | 0.00 | 0.10 |
| Ex. 2 | 0.02 | 0.02 | 0.03 | 0.00 | 0.01 | 0.12 |
| Ex. 3 | 0.02 | 0.02 | 0.03 | 0.02 | 0.01 | 0.15 |
| Ex. 4 | 0.02 | 0.02 | 0.03 | 0.02 | 0.02 | 0.10 |
| Ex. 5 | 0.02 | 0.02 | 0.02 | 0.01 | 0.01 | 0.09 |
| Ex. 6 | 0.02 | 0.02 | 0.04 | 0.02 | 0.00 | 0.17 |
| Ex. 7 | 0.02 | 0.01 | 0.03 | 0.00 | 0.01 | 0.11 |
| Ex. 8 | 0.02 | 0.02 | 0.03 | 0.01 | 0.01 | 0.12 |
| Comp. Ex. 1 | 0.03 | 0.02 | 0.04 | 0.06 | 0.07 | 0.23 |
| Comp. Ex. 2 | 0.02 | 0.02 | 0.02 | 0.00 | 0.01 | 0.11 |
| Comp. Ex. 3 | 0.02 | 0.02 | 0.06 | 0.11 | 0.09 | 0.29 |
| Comp. Ex. 4 | 0.02 | 0.02 | 0.05 | 0.09 | 0.08 | 0.26 |
| Comp. Ex. 5 | 0.02 | 0.01 | 0.02 | 0.00 | 0.00 | 0.10 |
| Comp. Ex. 6 | 0.03 | 0.02 | 0.07 | 0.15 | 0.12 | 0.40 |
| Comp. Ex. 7 | 0.03 | 0.01 | 0.03 | 0.18 | 0.15 | 0.41 |

TABLE 8

Amount of levocetirizine related compounds under accelerated storage condition for 6 months

| | Accelerated (6 months) | | | | | |
|---|---|---|---|---|---|---|
| Formulation | Related compound A (%) | Related compound B (%) | Related compound E (%) | Unknown related compound RRT = 0.59 (%) | Unknown related compound RRT = 0.64 (%) | Total (%) |
| Ex. 1 | 0.05 | 0.07 | 0.08 | 0.07 | 0.03 | 0.42 |
| Ex. 2 | 0.05 | 0.06 | 0.09 | 0.08 | 0.05 | 0.43 |
| Ex. 3 | 0.05 | 0.07 | 0.09 | 0.09 | 0.15 | 0.57 |
| Ex. 4 | 0.08 | 0.06 | 0.09 | 0.10 | 0.21 | 0.55 |
| Ex. 5 | 0.06 | 0.08 | 0.08 | 0.09 | 0.15 | 0.48 |
| Ex. 6 | 0.05 | 0.05 | 0.07 | 0.11 | 0.17 | 0.46 |
| Ex. 7 | 0.07 | 0.06 | 0.07 | 0.09 | 0.11 | 0.41 |
| Ex. 8 | 0.04 | 0.07 | 0.08 | 0.06 | 0.08 | 0.35 |

TABLE 8-continued

Amount of levocetirizine related compounds under accelerated storage condition for 6 months

| Formulation | Accelerated (6 months) | | | | | |
|---|---|---|---|---|---|---|
| | Related compound A (%) | Related compound B (%) | Related compound E (%) | Unknown related compound RRT = 0.59 (%) | Unknown related compound RRT = 0.64 (%) | Total (%) |
| Comp. Ex. 1 | 0.13 | 0.07 | 0.13 | 0.12 | 0.37 | 0.94 |
| Comp. Ex. 2 | 0.05 | 0.06 | 0.08 | 0.07 | 0.04 | 0.45 |
| Comp. Ex. 3 | 0.22 | 0.34 | 0.43 | 0.62 | 0.43 | 2.07 |
| Comp. Ex. 4 | 0.06 | 0.29 | 0.35 | 0.34 | 0.28 | 1.26 |
| Comp. Ex. 5 | 0.05 | 0.06 | 0.08 | 0.09 | 0.04 | 0.35 |
| Comp. Ex. 6 | 0.31 | 0.38 | 0.49 | 0.65 | 0.37 | 2.20 |
| Comp. Ex. 7 | 0.43 | 0.55 | 0.74 | 0.77 | 0.51 | 3.12 |

TABLE 9

Initial amount of montelukast related compounds

| Formulation | Initial | | |
|---|---|---|---|
| | Montelukast sulfoxide (%) | Montelukast cis-isomer (%) | Total (%) |
| Ex. 1 | 0.08 | 0.01 | 0.15 |
| Ex. 2 | 0.08 | 0.02 | 0.15 |
| Ex. 3 | 0.08 | 0.03 | 0.16 |
| Ex. 4 | 0.08 | 0.04 | 0.16 |
| Ex. 5 | 0.09 | 0.02 | 0.16 |
| Ex. 6 | 0.09 | 0.02 | 0.16 |
| Ex. 7 | 0.08 | 0.03 | 0.15 |
| Ex. 8 | 0.08 | 0.03 | 0.15 |
| Comp. Ex. 1 | 0.08 | 0.03 | 0.16 |
| Comp. Ex. 2 | 0.08 | 0.02 | 0.15 |
| Comp. Ex. 3 | 0.12 | 0.05 | 0.20 |
| Comp. Ex. 4 | 0.09 | 0.04 | 0.17 |
| Comp. Ex. 5 | 0.08 | 0.02 | 0.16 |
| Comp. Ex. 6 | 0.10 | 0.04 | 0.17 |
| Comp. Ex. 7 | 0.09 | 0.03 | 0.16 |

TABLE 10

Amount of montelukast related compounds under accelerated storage condition for 6 months

| Formulation | Accelerated (6 months) | | |
|---|---|---|---|
| | Montelukast sulfoxide (%) | Montelukast cis-isomer (%) | Total (%) |
| Ex. 1 | 0.15 | 0.06 | 0.28 |
| Ex. 2 | 0.14 | 0.06 | 0.28 |
| Ex. 3 | 0.19 | 0.09 | 0.42 |
| Ex. 4 | 0.18 | 0.07 | 0.35 |
| Ex. 5 | 0.14 | 0.05 | 0.25 |
| Ex. 6 | 0.12 | 0.05 | 0.23 |
| Ex. 7 | 0.17 | 0.11 | 0.32 |
| Ex. 8 | 0.14 | 0.06 | 0.27 |
| Comp. Ex. 1 | 0.32 | 0.13 | 0.59 |
| Comp. Ex. 2 | 0.15 | 0.07 | 0.30 |
| Comp. Ex. 3 | 0.38 | 0.17 | 0.67 |
| Comp. Ex. 4 | 0.35 | 0.14 | 0.63 |
| Comp. Ex. 5 | 0.15 | 0.06 | 0.28 |
| Comp. Ex. 6 | 0.29 | 0.15 | 0.55 |
| Comp. Ex. 7 | 0.42 | 0.27 | 0.73 |

As shown in Tables 7 to 10, and FIGS. 1 to 9, the complex granule formulations prepared in Examples 1 to 8 comprising both cyclodextrin and the alkalinizing agent resulted in insignificant changes under the accelerated test condition for 6 months, and thus exhibited exceptionally good storage stability.

However, the complex granule formulations prepared in Comparative Examples 1 and 3, which contain neither cyclodextrin nor the alkalinizing agent, showed about 2- to 5-fold increased related compounds as compared to the complex granule formulations prepared in Examples 1 to 8. This result shows that allowing active ingredients to form clathrate with cyclodextrin and using an alkalinizing agent can improve stability of levocetirizine and montelukast in the complex granules.

Also, the complex granule formulation of Comparative Example 2, which used the alkalinizing agent meglumine in an amount greater than 0.6 wt % based on the total weight of levocetirizine or montelukast granular part, did not show any additional improvement in stability. The complex granule formulation of Comparative Example 4, which used cyclodextrin in an amount less than 3 wt % based on the total weight of levocetirizine or montelukast granular part, resulted in poor stability due to lack of clathrate formulation. Moreover, when sodium hydroxide was used as an alkalinizing agent, e.g., Comparative Example 6, the stability of the formulation deteriorated as compared to formulations using other alkalinizing agents.

Meanwhile, the formulation of Comparative Example 7, which had granules comprising both levocetirizine and montelukast instead of having separately formed levocetirizine granular part and montelukast part, resulted in noticeably low stability. It is considered that the low stability is caused by undesirable interaction between levocetirizine and montelukast which promoted generation of related compounds. Thus, it would be preferable to granulate each active ingredient separately to form clathrate complexes.

Experimental Example 2: Sensory Test

A bitter test was conducted on complex granule formulations of Examples 1 to 6 and Comparative Examples 2 to 5. Ten healthy adult males were given one dose of the complex granule formulation (1 g as a complex granule), and the degree of bitterness was evaluated right after administration and 1 minute after the administration. The evaluation was measured in accordance with the following criteria and averaging the results:

0: no bitterness at all
1: almost no bitterness
2: somewhat bitter
3: bitter
4: strongly bitter.

TABLE 11

| Subject | Ex. 1 | Ex. 2 | Ex. 3 | Ex. 4 | Ex. 5 | Ex. 6 | Co. Ex. 2 | Co. Ex. 3 | Co. Ex. 4 | Co. Ex. 5 |
|---|---|---|---|---|---|---|---|---|---|---|
| 1 | 0 | 1 | 0 | 0 | 1 | 0 | 2 | 3 | 3 | 1 |
| 2 | 0 | 0 | 1 | 2 | 0 | 0 | 3 | 4 | 4 | 3 |
| 3 | 1 | 1 | 0 | 1 | 0 | 0 | 1 | 4 | 3 | 1 |
| 4 | 0 | 0 | 0 | 2 | 0 | 1 | 4 | 3 | 2 | 3 |
| 5 | 0 | 1 | 0 | 2 | 1 | 1 | 2 | 3 | 4 | 4 |
| 6 | 1 | 0 | 1 | 1 | 1 | 0 | 1 | 4 | 1 | 1 |
| 7 | 0 | 0 | 0 | 0 | 1 | 0 | 4 | 3 | 2 | 4 |
| 8 | 1 | 1 | 1 | 1 | 1 | 0 | 2 | 4 | 4 | 1 |
| 9 | 0 | 0 | 0 | 2 | 0 | 0 | 1 | 4 | 3 | 4 |
| 10 | 1 | 0 | 1 | 1 | 0 | 1 | 3 | 3 | 2 | 4 |
| Avg. | 0.4 | 0.4 | 0.4 | 1.2 | 0.5 | 0.3 | 2.3 | 3.5 | 2.8 | 2.6 |
| Dev. | 0.52 | 0.52 | 0.52 | 0.79 | 0.53 | 0.48 | 1.16 | 0.53 | 1.03 | 1.43 |

As shown in Table 11 above, the degree of bitterness of the formulation prepared in Comparative Example 3 which did not employ cyclodextrin, was significantly higher than those of formulation which had cyclodextrin. Also, the effectiveness in masking bitter taste increased up to a certain point as the amount of cyclodextrin was increased; and then, as can be seen in Comparative Example 5, the masking property deteriorated because cyclodextrin was not completely dissolved during the preparation process and failed to mask the bitter taste. Further, when the alkalinizing agent meglumine was used in an excessive amount, e.g., the formulation of Comparative Example 2, the subjects were able to sense unpleasant taste of meglumine, and thus it was not desirable.

Therefore, it is preferable to use cyclodextrin and the alkalinizing agent in suitable amounts for effective masking of bitter taste.

Experimental Example 3: Bioavailability Test

The complex granule formulations of Examples 1 and Comparative Examples 3 were tested for their bioavailability of levocetirizine and montelukast in rats. Twelve healthy male Sprague-Dawley rats (Sprague Dawley Inc., U.S.A.) were randomly assigned into two groups, and studied in a cross over manner. Drug concentrations of the drugs in the blood plasma were evaluated, and pharmacokinetic parameters were analyzed with WinNonlin® (Phoenix®) by using the drug concentrations over time. The results are shown in Tables 12 and 13.

Figure 10:
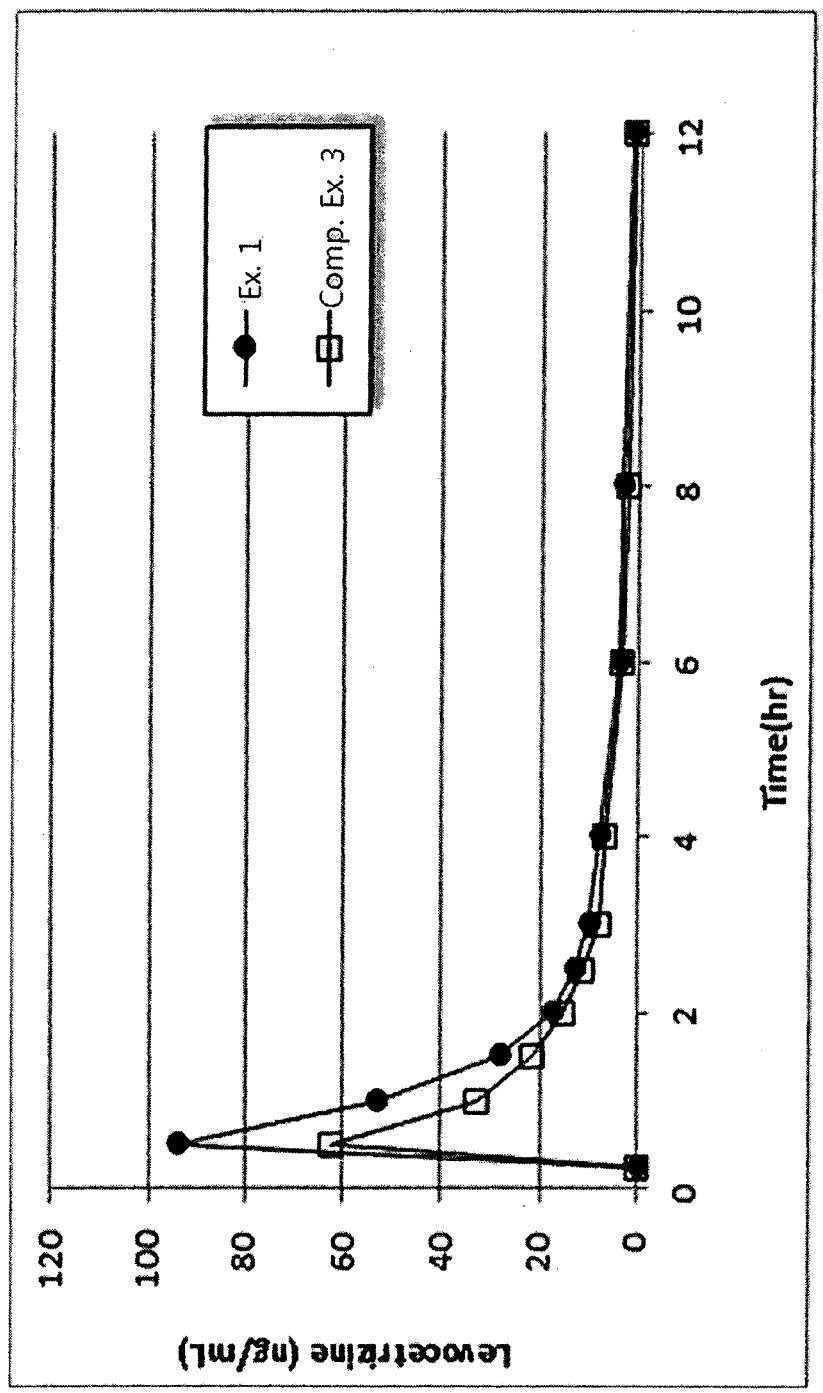
FIG. 10 shows the change in bioavailability of levocetirizine, measured from complex granule formulations obtained in Example 1 and Comparative Example 3.
Figure 11:
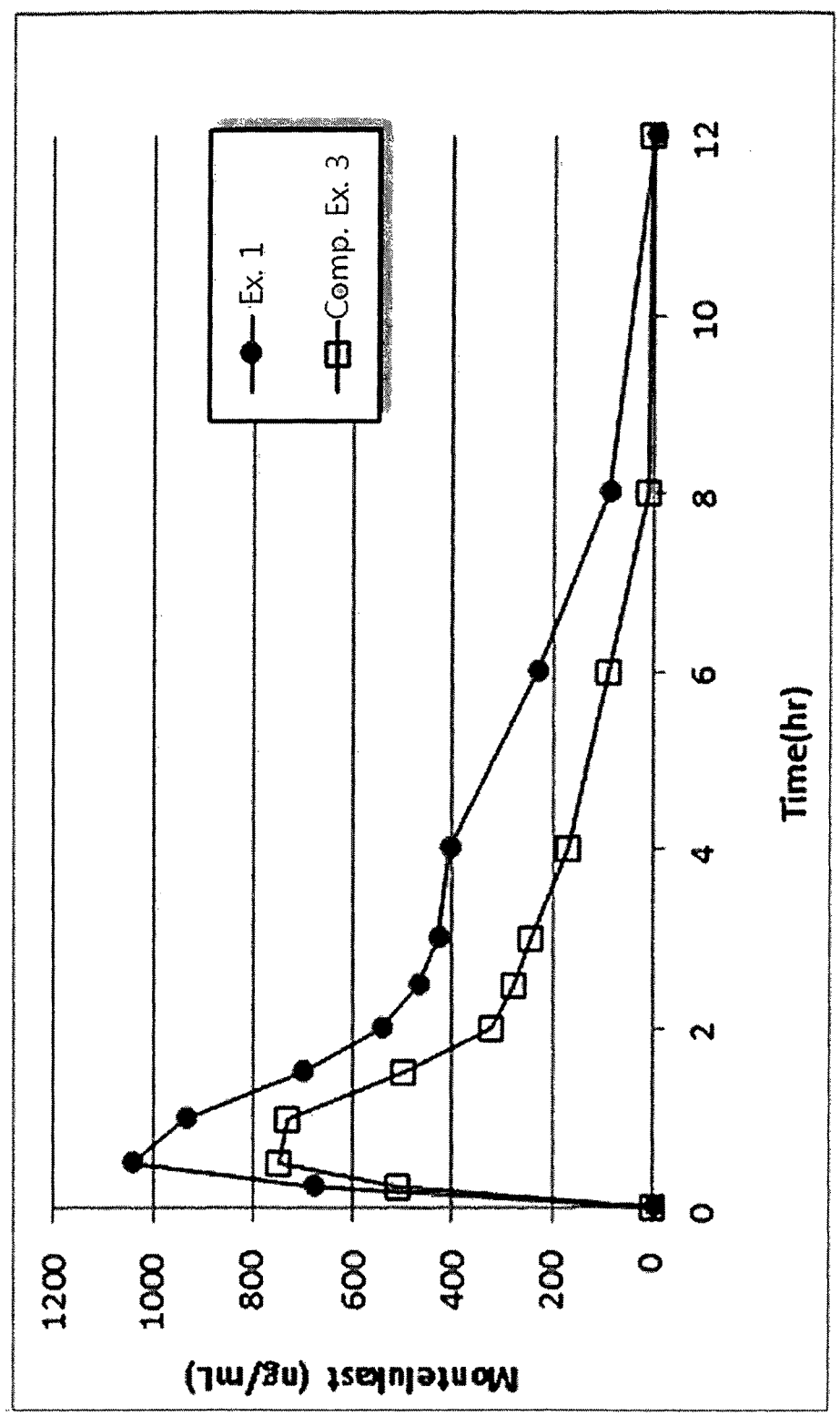
FIG. 11 shows the change in bioavilability of montelukast, measured from complex granule formulations obtained in Example 1 and Comparative Example 3.

FIGS. 10 and 11 show linear graphic profiles of the average plasma concentrations of levocetirizine (ng/mL) and montelukast (ng/mL) versus time (hr), respectively.

TABLE 12

| | Levocetirizine | |
|---|---|---|
| Parameters | Ex. 1 | Comp. Ex. 3 |
| $AUC_{0-12}$ (ng · hr/mL) | 95.9 ± 12.5 | 69.9 ± 15.1 |
| $C_{max}$ (ng/mL) | 94.3 ± 8.9 | 62.4 ± 7.3 |
| $T_{max}$ (hr) | 0.25 ± 0.41 | 0.28 ± 0.39 |

TABLE 13

| | Montelukast | |
|---|---|---|
| Parameters | Ex. 1 | Comp. Ex. 3 |
| $AUC_{0-24}$ (ng · hr/mL) | 3421.8 ± 871.2 | 1934.7 ± 766.8 |
| $C_{max}$ (ng/mL) | 1044.1 ± 279.0 | 749.7 ± 197.1 |
| $T_{max}$ (hr) | 0.68 ± 0.31 | 0.65 ± 0.23 |

As shown in Tables 12 and 13, and FIGS. 10 and 11, the complex granule formulation of Example 1 comprising cyclodextrin demonstrated superior bioavailabilities of montelukast and levocetirizine as compared to the formulation of Comparative Example which did not contain any cyclodextrin. Therefore, it was found that cyclodextrin can be added to a complex granule formulation to increase solubilities of montelukast and levocetirizine, and ultimately to improve bioavailabilities of said active ingredients.

What is claimed is:

1. A complex granule formulation comprising:
   (a) a first granular part comprising levocetirizine or a pharmaceutically acceptable salt thereof, cyclodextrin or a derivative thereof, and an alkalinizing agent; and
   (b) a second granular part comprising montelukast or a pharmaceutically acceptable salt thereof, cyclodextrin or a derivative thereof, and an alkalinizing agent,
   wherein the cyclodextrin or its derivative is β-cyclodextrin or hydroxypropyl β-cyclodextrin.

2. The complex granule formulation of claim 1, wherein the cyclodextrin or its derivative is contained in an amount of 3 to 7 wt % based on the total weight of each granular part.

3. The complex granule formulation of claim 1, wherein the alkalinizing agent is selected from the group consisting of meglumine, sodium bicarbonate, sodium carbonate monohydrate, ammonia water, sodium citrate, dried sodium carbonate, and a mixture thereof.

4. The complex granule formulation of claim 1, wherein the alkalinizing agent is contained in an amount of 0.2 to 0.6 wt % based on the total weight of each granular part.

5. The complex granule formulation of claim 1, wherein each of the first and the second granular parts further comprises a pharmaceutically acceptable additive.

6. The complex granule formulation of claim 5, wherein the pharmaceutically acceptable additive is selected from the group consisting of a diluent, a sweetener, a flavor, a colorant, a binder, and a mixture thereof.

7. The complex granule formulation of claim 1, wherein the complex granule formulation is used for the treatment of allergic rhinitis or asthma.

8. The complex granule formulation of claim 7, wherein the allergic rhinitis is selected from the group consisting of rhinorrhea, nasal obstruction, nasal itching, sneezing and ocular pruritis.

* * * * *